US011172974B2

(12) United States Patent
Lalonde (10) Patent No.: US 11,172,974 B2
(45) Date of Patent: *Nov. 16, 2021

(54) METHOD OF USING TIME TO EFFECT (TTE) TO ESTIMATE THE OPTIMUM CRYODOSE TO APPLY TO A PULMONARY VEIN

(71) Applicant: Medtronic CryoCath LP, Toronto (CA)

(72) Inventor: Jean-Pierre Lalonde, Candiac (CA)

(73) Assignee: Medtronic CryoCath LP

( * ) Notice: Subject to any disclaimer, the term of this patent is extended or adjusted under 35 U.S.C. 154(b) by 408 days.

This patent is subject to a terminal disclaimer.

(21) Appl. No.: 16/281,777

(22) Filed: Feb. 21, 2019

(65) Prior Publication Data
US 2019/0175244 A1 Jun. 13, 2019

Related U.S. Application Data

(63) Continuation of application No. 15/091,865, filed on Apr. 6, 2016, now Pat. No. 10,251,692.

(51) Int. Cl.
*A61B 18/12* (2006.01)
*A61B 18/02* (2006.01)
(Continued)

(52) U.S. Cl.
CPC .... *A61B 18/02* (2013.01); *A61B 2017/00053* (2013.01); *A61B 2018/0022* (2013.01);
(Continued)

(58) Field of Classification Search
CPC ............ A61B 18/02; A61B 2018/0022; A61B 2018/00357; A61B 2018/00577;
(Continued)

(56) References Cited

U.S. PATENT DOCUMENTS

| 5,891,134 A | * | 4/1999 | Goble | A61B 18/08 |
| | | | | 606/27 |
| 6,805,128 B1 | * | 10/2004 | Pless | A61B 18/02 |
| | | | | 128/898 |

(Continued)

FOREIGN PATENT DOCUMENTS

| CN | 101528144 A | 9/2009 |
| CN | 101601894 A | 12/2009 |

(Continued)

OTHER PUBLICATIONS

Notice of the First Office Action for corresponding Chinese Application No. 201780022296.9, dated Jun. 28, 2020, 18 pages.

(Continued)

*Primary Examiner* — Daniel W Fowler
(74) *Attorney, Agent, or Firm* — Christopher & Weisberg, P.A.

(57) ABSTRACT

A system and method for determining the optimum dose of cryotreatment to an area of target tissue to achieve isolation based on the time to effect (TTE). The system may generally include a treatment device, a sensing device, and a processor programmed to calculate the optimum dose of cryotreatment, in seconds, based on TTE. The TTE may be based on electrical signals received by the processor from the sensing device. The processor may be further programmed to automatically terminate a cryoablation procedure when the optimum dose of cryotreatment has elapsed. The optimum dose of cryotreatment may be the time, in seconds, it takes to achieve isolation, which may be the time it takes for an area of tissue to reach approximately −20° C.

15 Claims, 6 Drawing Sheets

(51) Int. Cl.
    *A61B 18/00*    (2006.01)
    *A61B 17/00*    (2006.01)
(52) U.S. Cl.
    CPC .............. *A61B 2018/00357* (2013.01); *A61B 2018/00577* (2013.01); *A61B 2018/00672* (2013.01); *A61B 2018/00744* (2013.01); *A61B 2018/00761* (2013.01); *A61B 2018/00839* (2013.01); *A61B 2018/0212* (2013.01)
(58) Field of Classification Search
    CPC ........... A61B 2018/00672; A61B 2018/00744; A61B 2018/00761; A61B 2018/00839; A61B 2018/0212
    See application file for complete search history.

(56) References Cited

U.S. PATENT DOCUMENTS

| | | | |
|---|---|---|---|
| 8,480,664 | B2 | 7/2013 | Watson et al. |
| 2003/0153905 | A1* | 8/2003 | Edwards ............ A61B 18/1492 606/41 |
| 2006/0122590 | A1* | 6/2006 | Bliweis ................ A61B 18/082 606/24 |
| 2010/0179527 | A1 | 7/2010 | Watson et al. |
| 2010/0191142 | A1* | 7/2010 | Paul ........................ A61B 5/015 600/549 |
| 2012/0035601 | A1 | 2/2012 | Wittenberger |
| 2013/0261368 | A1* | 10/2013 | Schwartz .............. A61B 18/06 600/1 |
| 2015/0018809 | A1 | 1/2015 | Mihalik |
| 2015/0119868 | A1 | 4/2015 | Lalonde et al. |
| 2015/0157382 | A1 | 6/2015 | Avitall et al. |
| 2015/0282859 | A1 | 10/2015 | Bencini et al. |

FOREIGN PATENT DOCUMENTS

| | | |
|---|---|---|
| CN | 102106753 A | 6/2011 |
| CN | 103705302 A | 4/2014 |
| WO | 2013009669 A2 | 1/2013 |

OTHER PUBLICATIONS

China National Intellectual Property Administration, Notice of the Second Office Action and Search Report, for corresponding Application No. 201780022296.9, dated Mar. 4, 2021, 13 pages.
International Search Report and Written Opinion dated Jun. 29, 2017 for International Application No. PCT/CA2017/050318 International Filing Date—Mar. 10, 2017 consisting of 7 pages.
Choi, Jeunghwan, Cooling rate dependent biophysical and viability response shift with attachment state in human dermal fibroblast cells, Cryobiology 63 (2011) 285-291.
Choi, Jeunghwan, Review of biomaterial thermal property measurements in the cryogenic regime and their use for prediction of equilibrium and non-equilibrium freezing applications in cryobiology, Cryobiology 60 (2010) 52-70.
Uwe Dorwarth, et al., Pulmonary Vein Electrophysiology During Cryoballoon Ablation as a Predictor for Procedural Success, J Interv Card Electrophysiol (2011) 32:205-211.
Yi Gang, et al., Evaluation of the Achieve Mapping Catheter in Cryoablation for Atrial Fibrillation: A Prospective Randomized Trial, J Interv Card Electrophysiol (2016) 45:179-187.
Supplementary European Search Report dated Oct. 8, 2019 for corresponding European Application No. EP17 77 8501; 11 pages.

* cited by examiner

METHOD OF USING TIME TO EFFECT (TTE) TO ESTIMATE THE OPTIMUM CRYODOSE TO APPLY TO A PULMONARY VEIN

CROSS-REFERENCE TO RELATED APPLICATION

This application is a continuation of U.S. application Ser. No. 15/091,865, filed Apr. 6, 2016, titled METHOD OF USING TIME TO EFFECT (TTE) TO ESTIMATE THE OPTIMUM CRYODOSE TO APPLY TO A PULMONARY VEIN.

STATEMENT REGARDING FEDERALLY SPONSORED RESEARCH OR DEVELOPMENT n/a

TECHNICAL FIELD

The present invention relates to a system and method for determining the optimum dose of cryotreatment to an area of target tissue to achieve isolation based on the time to effect (TTE).

BACKGROUND

Cryotreatment, particularly cryoablation, is frequently used to treat a variety of cardiac arrhythmias, including atrial fibrillation. Many cardiac arrhythmias are caused by or involve the conduction of aberrant electrical currents through cardiac tissue. During cryoablation, tissue is cooled by a cryotreatment catheter until the aberrant electrical conduction is eliminated or otherwise deemed to be ameliorated. For example, some aberrant electrical currents may originate from within one or more pulmonary veins. In this case, the pulmonary vein ostium and/or antrum may be cooled until the pulmonary vein(s) is/are isolated from the left atrium or other cardiac tissue.

The time to effect (TTE) may be defined as the time it takes for an area of cardiac tissue to stop conducting electricity. This is known to occur when all the conducting tissue around an ablation site has reached a temperature below approximately +23° C., at which temperature the cells do not repolarize, and it can happen only once the deepest conducting fiber of tissue has reached that temperature. Therefore, a longer time to achieve TTE indicates the presence of fibers that are more difficult to cool, and this also correlates to a longer time to achieve permanent isolation (TTI). Both TTE and TTI may be correlated to each other according to the thickness of the tissue to be ablated (or to be more precise, where the deepest conducting fiber is located), such as the thickness of a target pulmonary vein, and/or according to the quality of ablation (such as surface contact, push force, alignment of the cryotreatment element with the tissue, quality of pulmonary vein occlusion, or the like). So, better contact quality and a thinner area of tissue results in a shorter time to achieve TTE and, therefore, the smaller the dose of thermal treatment.

When treating particular regions of tissue, it may be difficult to direct or control the depth of the cryoablation. For example, the reduction in tissue temperature may not be contained to the exact region or depth desired for treatment using currently known methods, and this often necessitates having to carefully monitor lesion formation and/or tissue temperature in real time, which can be difficult and imprecise, and/or having to assess lesion formation after a cryoablation procedure, which can result in unintended damage if not monitored during the procedure. Collateral damage to non-target tissue may result if a lesion extends too far or too deep beyond the target treatment area. Conversely, the procedure may not correct the aberrant electrical conduction if the treatment is not delivered for an adequate amount of time or at a sufficient tissue depth.

It is therefore desired to provide a system and method for predicting or determining the optimum dose of cryotreatment to an area of target tissue to achieve isolation based on the time to effect (TTE).

SUMMARY

The present invention advantageously provides a system and method for determining the optimum dose of cryotreatment to an area of target tissue to achieve isolation based on the time to effect (TTE). A cryoablation system may generally include a processor configured to receive mapping signals, calculate a time to effect (TTE) based on the received mapping signals, and determine a recommended cryoablation dose based on the TTE. The processor further be configured to determine a time to isolation (TTI) based on the TTE. The recommended cryoablation dose may be the amount of cryoablation, in seconds, required to achieve TTI. Further, TTI may be the time, in seconds, it takes for an area of tissue to reach −20° C. The processor may be configured to determine TTE is achieved when no mapping signals are received. Additionally or alternatively, the processor may be configured to determine TTE is achieved when a peak amplitude of the received mapping signals are reduced by half. Additionally or alternatively, the processor may be configured to determine TTE is achieved when a delay between adjacent peaks of the received mapping signals increases by approximately 20%. The system may further include a sensing device in communication with the processor, the sensing device including a plurality of mapping elements, each of the plurality of mapping elements being configured to transmit mapping signals to the processor. Each of the plurality of mapping elements may be configured to obtain mapping signals from an area of tissue. The sensing device further may include an elongate body having a proximal portion and a distal portion, each of the plurality of mapping elements being coupled to the elongate body distal portion. The system may also include a treatment device in communication with the processor, the treatment device including an elongate body having a proximal portion and a distal portion and a treatment element (for example, a balloon) coupled to the distal portion of the treatment device elongate body. The treatment device also may include a central lumen, and the sensing device elongate body may be longitudinally movable within the central lumen. Further, the processor may be configured to adjust a temperature of the treatment element based on the determined recommended cryoablation dose. For example, the processor may be configured to adjust a temperature of the treatment element by modifying a flow of coolant within the treatment element.

A cryoablation system may generally include: a cryotreatment device including a treatment element; a sensing device including a plurality of mapping elements, each of the plurality of mapping elements being configured to obtain mapping signals from an area of tissue; and a processor in communication with the cryotreatment device and the sensing device, the processor being programmed to: receive the mapping signals from the plurality of mapping elements;

calculate a time to effect (TTE) based on the received mapping signals; and determine a recommended cryoablation dose based on the TTE. The processor may also be programmed to determine a time to isolation (TTI) based on the TTE, the recommended cryoablation dose being the cryoablation time, in seconds, to achieve TTI. The TTI may be the time, in seconds, it takes for an area of tissue to reach −20° C., or may be the time, in seconds, it takes to achieve at least 75% cell death. The processor may also be programmed to add 60 seconds to the recommended cryoablation dose in order to achieve at least 85% cell death. Additionally or alternatively, the processor may be programmed to propose a second recommended cryoablation dose in order to achieve at least 95% cell death. The processor may be further programmed to deliver the second cryoablation dose after a warming period. The processor may be further programmed to determine a threshold period of time in which TTE is expected to occur. If the TTE does not occur until after this threshold period of time has elapsed, the recommended cryoablation dose may be based on an occurrence of TTE and/or the processor may generate a suggestion that the treatment element be repositioned.

A cryoablation system may generally include: a cryotreatment device including an elongate body having a proximal portion, a distal portion, a central lumen, and a treatment element coupled to the distal portion of the cryotreatment device elongate body; a sensing device including an elongate body having a proximal portion and a distal portion and a plurality of mapping elements coupled to the distal portion of the mapping device elongate body, each of the plurality of mapping elements being configured to obtain mapping signals from an area of tissue, the elongate body of the sensing device being longitudinally movable within the central lumen of the cryotreatment device; and a processor in communication with the cryotreatment device and the sensing device, the processor being programmed to: receive the mapping signals from the plurality of mapping elements; calculate a time to effect (TTE) based on the received mapping signals, TTE being achieved when one or more peak amplitudes of the received mapping signals decreases by half or a time between two or more peak amplitudes of the received mapping signals increases by more than 20%; correlating the TTE to a time to isolation (TTI), the TTI being the time it takes an area of tissue to reach approximately −20° C., which generally speaking corresponds to about 75% cell death or greater within the area of tissue; and determine a recommended cryoablation dose based on the TTI. The processor may also be programmed to add 60 seconds to the determined recommended cryoablation dose in order to achieve at least 85% cell death within the area of tissue.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
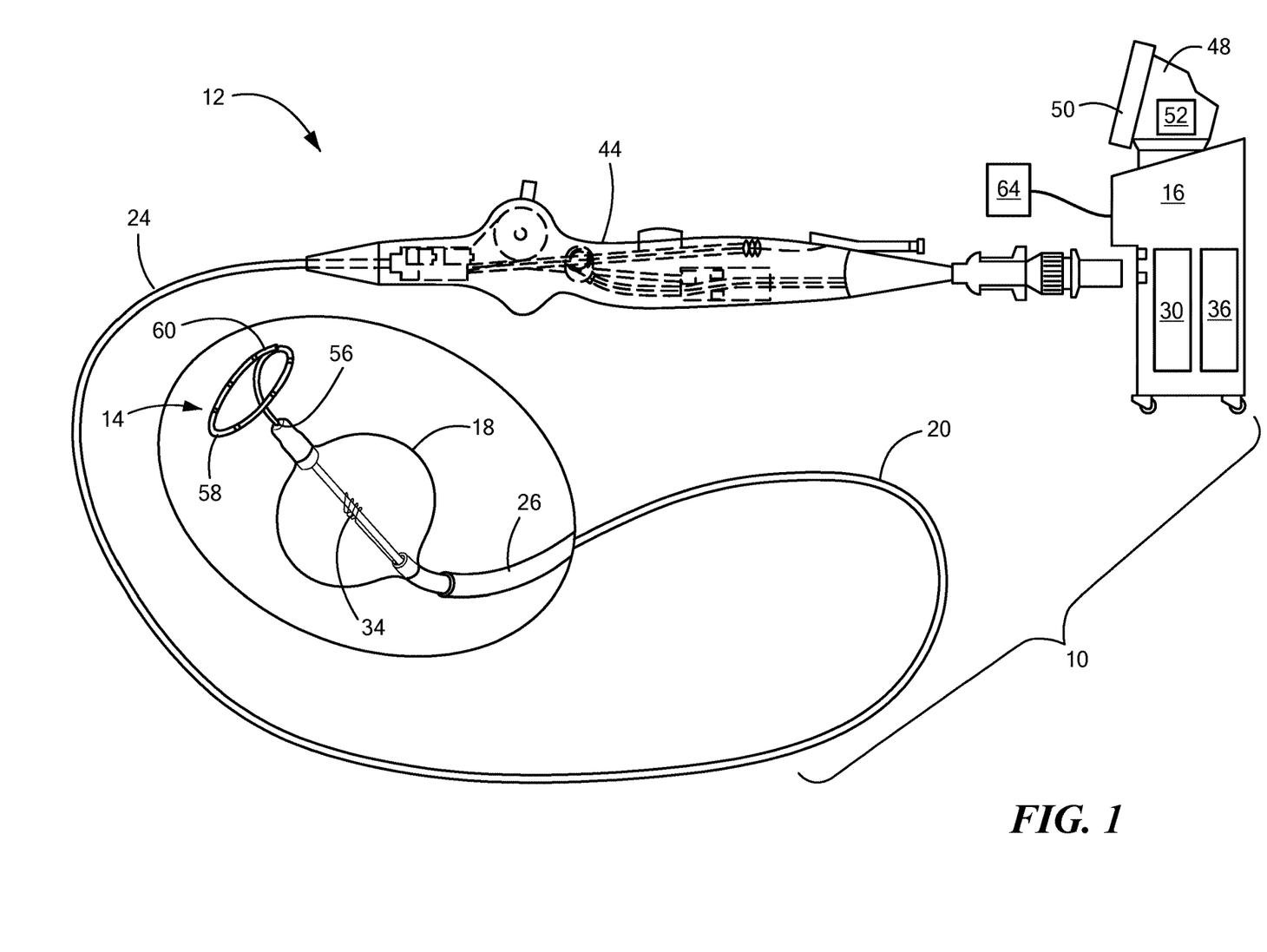
FIG. 1 shows an exemplary cryoablation system configured to determine an optimum dose of cryoablation for an area of target tissue.

The present invention advantageously provides systems and methods to determine or predict an optimum dose of cryotreatment to an area of target tissue, based on time to effect (TTE), to achieve electrical isolation. In particular, as shown in the accompanying figures in which like reference designators refer to like components, a medical system is shown in FIG. 1, generally designated as '10'. The medical system 10 may generally include a cryoablation device 12, a sensing device 14, and one or more control units 16 coupled to the cryoablation device 12 and/or the sensing device 14.

The cryoablation device 12 may include a medical probe, a catheter, or other instrument, and may generally include one or more diagnostic or treatment elements 18 for energetic or other therapeutic interaction between the device 12 and a treatment site. The treatment element(s) 18 may deliver, for example, cryogenic therapy, radiofrequency energy, or other energetic transfer with a tissue area in proximity to the treatment region(s), including cardiac tissue. In particular, the one or more treatment elements 18 may be configured to reduce the temperature of adjacent tissue in order to perform cryotreatment and/or cryoablation. For example, the treatment region(s) 18 may include one or more balloons (as shown in FIG. 1) within which a cryogenic coolant may be circulated in order to reduce the temperature of the balloon. Additionally, the treatment region(s) 18 may include other thermally and/or electrically-conductive components, such as one or more electrodes in communication with the control unit 16.

The cryoablation device 12 may include an elongate body 20 passable through a patient's vasculature and/or positionable proximate to a tissue region for diagnosis or treatment, such as a catheter, sheath, or intravascular introducer. The elongate body 20 may define a proximal portion 24 and a distal portion 26, and may further include one or more lumens disposed within the elongate body 20 that provide mechanical, electrical, and/or fluid communication between the proximal portion 24 of the elongate body 20 and the distal portion 26 of the elongate body 20. Further, the one or more treatment regions 18 (such as the balloon shown in FIG. 1) may be coupled to the elongate body distal portion 26.

During operation, coolant may flow from a coolant supply 30 through a coolant delivery conduit within the cryoablation device elongate body 20 to the distal portion 26, where the coolant may then enter the interior of a treatment region 18, such as through one or more nozzles, orifices, or other flow control elements 31, where the coolant may expand to cool the treatment region 18. Expanded coolant may then pass from the interior of the treatment region 18 to a coolant recovery reservoir 36 and/or scavenging system through a coolant recovery conduit.

The cryoablation device 12 may further include a handle 44 coupled to the elongate body proximal portion 24, and the handle 44 may include one or more steering or deflection components for manipulating the elongate body 20, the one or more treatment regions 18, and/or additional components of the cryoablation device 12. The handle 44 may also include connectors that are matable directly or indirectly to the control unit 16 to establish communication between the one or more components of the cryoablation device 12 with one or more components of the control unit 16, as described herein. For example, in an exemplary system, the coolant supply 30, coolant recovery reservoir 36, and/or one or more alternative energy sources to supply the selected modality of treatment to the treatment region(s) 18 (such as, for example, a radiofrequency generator, ultrasound generator, light sources, or the like) as well as various control mechanisms for the system 10 may be housed in the control unit 16. The control unit 16 may also include one or more computers 48 having one or more displays 50 and processors and/or software modules 52, and the one or more processors 52 may be programmed or programmable to execute the automated operation and performance of the features, sequences, or procedures described herein. It will be understood that one or more system components may be physically located outside of the control unit 16; however, any system components that are not part of the cryoablation device 12 or the sensing device 14 may be referred to herein as being located within the control unit 16 for simplicity.

The system 10 may further include a sensing device 14, which may also be referred to as a mapping device, for obtaining data from the target tissue, such as mapping signals, electrograms (for example, pulmonary vein potentials), monophasic action potentials, or the like. For example, the sensing device 14 shown in FIG. 1 may be configured to obtain pulmonary vein potentials, similar to the ACHIEVE® Mapping Catheter (Medtronic, Inc., Minneapolis, Minn.). The sensing device 14 may be used for the stimulation, measuring and/or monitoring of a physiological condition of a patient, as well as subsequent triggering or actuation of one or more predetermined, automated protocols or procedures in response to the monitored/measured condition.

The sensing device 14 may be longitudinally movable within a hollow central lumen 56 of the elongate body 20 and may be extendable beyond the distal end of the elongate body 20. The sensing device 14 may include one or more mapping or sensing electrodes 58, and the distal portion 60 of the sensing device 14 may be flexible such that it may be manipulated into a variety of configurations to adapt to the patient's anatomy. As a non-limiting example, the sensing device distal portion 60 may be manipulated using one or more steering elements into a loop or lasso configuration as shown in FIG. 1. Signals from the patient's tissue may be obtained by the sensing device electrodes 58 before, during, or after a cryotreatment procedure. Further, the sensing device may be in communication with the control unit 16 such that signals obtained by the electrodes 58 may be transmitted to the control unit 16 for processing and analysis.

The cryoablation device 12 and/or control unit 16 may also include one or more sensors to monitor the operating parameters throughout the system 10, including for example, pressure, temperature, flow rates, volume, or the like in the control unit 16, and/or the cryoablation device 12. For example, the cryoablation device 12 may further include one or more temperature and/or pressure sensors (not shown) proximate the treatment region(s) 18 for monitoring, recording or otherwise conveying measurements of conditions within the cryoablation device 12 or the ambient environment at the distal portion of the cryoablation device 12. The sensor(s) may be in communication with the control unit 16 for initiating or triggering one or more alerts or therapeutic delivery modifications during operation of the cryoablation device 12.

Figure 2A:
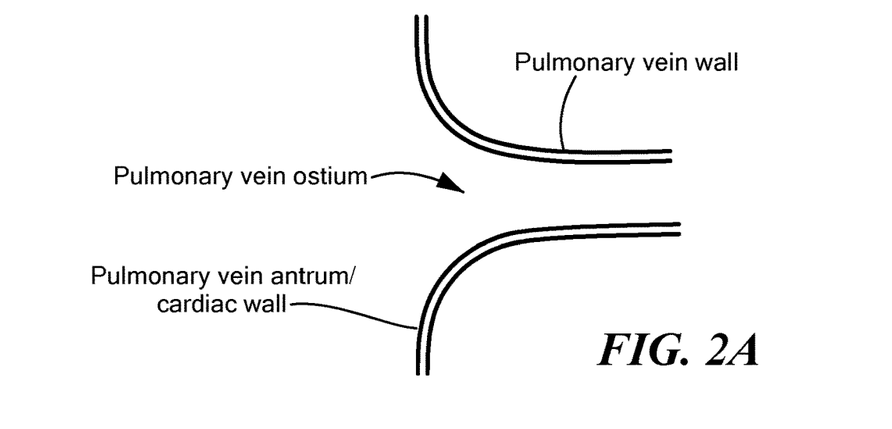
FIGS. 2A-2C show cross-sectional views of exemplary pulmonary veins of varying thicknesses.
Figure 2B:
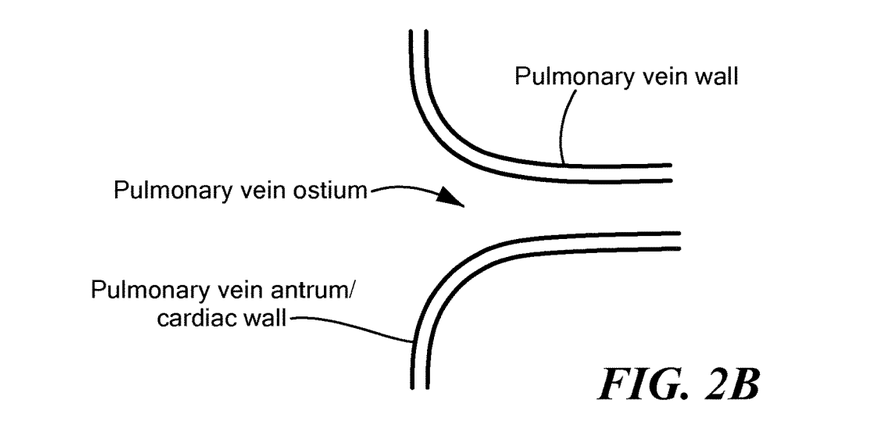
Figure 2C:
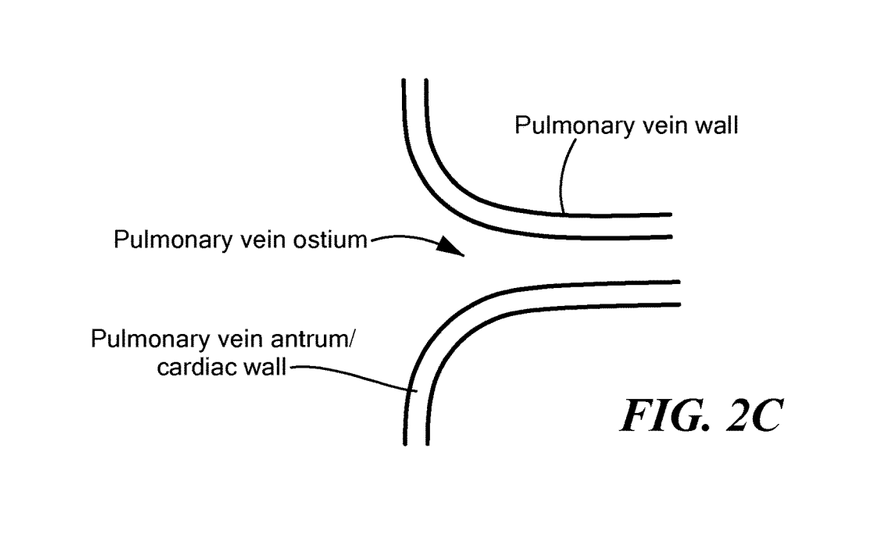

Referring now to FIGS. 2A-2C, cross-sectional views of exemplary pulmonary veins of varying thicknesses are shown. As will be discussed in more detail below, the thickness of an area of target tissue or the depth at which the deepest conducting fiber is located may affect the dose required to achieve isolation. Pulmonary veins are shown in FIGS. 2A-2C for illustration; however, it will be understood that these same principles may apply to the depth of conducting fibers in other areas of tissue as well. FIG. 2B shows a pulmonary vein having walls that are of "normal" or "standard" thickness, whereas FIG. 2A shows a pulmonary vein having walls that are comparatively thinner and FIG. 2C shows a pulmonary vein having walls that are comparatively thicker.

Figure 3A:
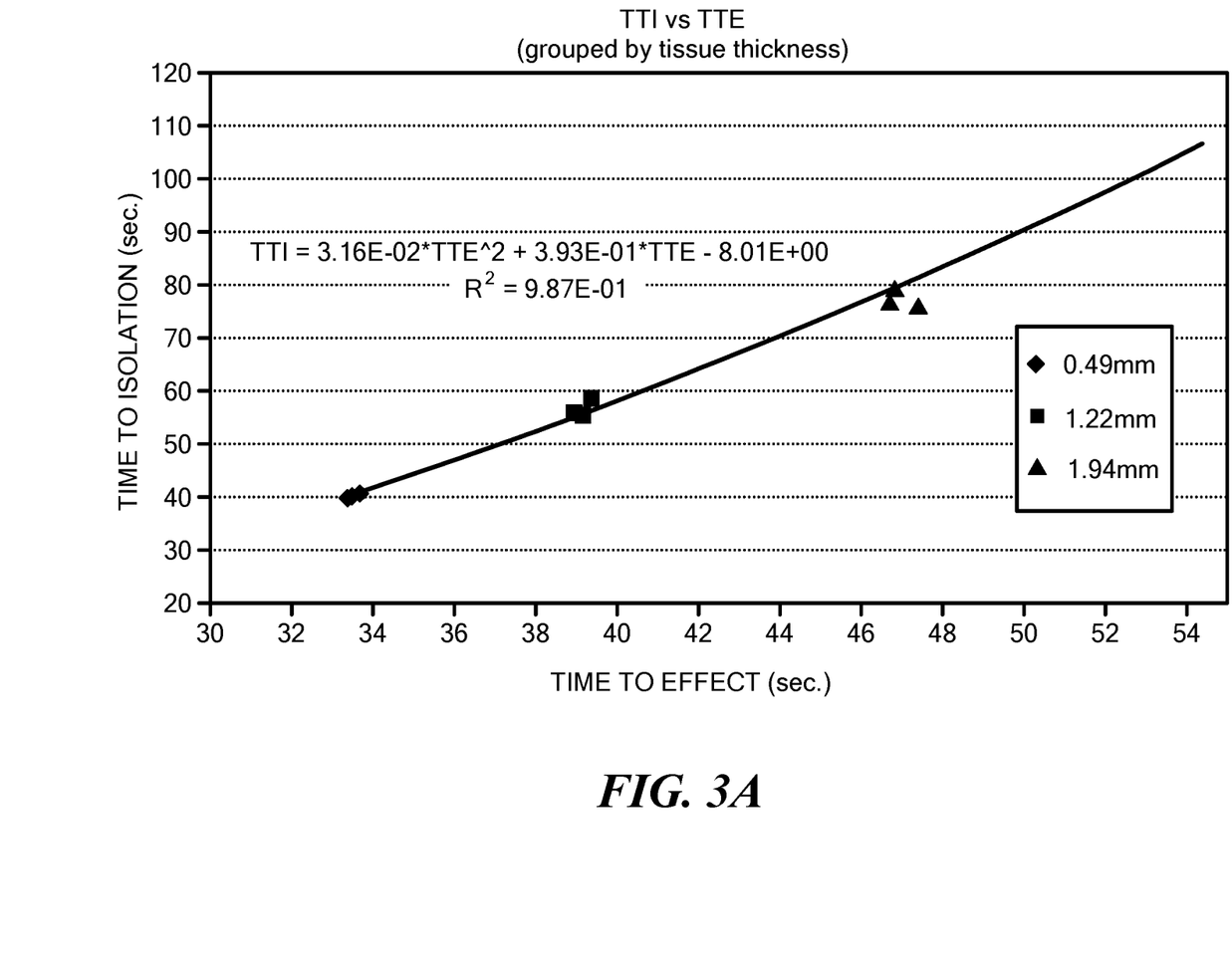
FIG. 3A shows a chart comparing exemplary TTE and TTI data, with data grouped according to tissue thickness.
Figure 3B:
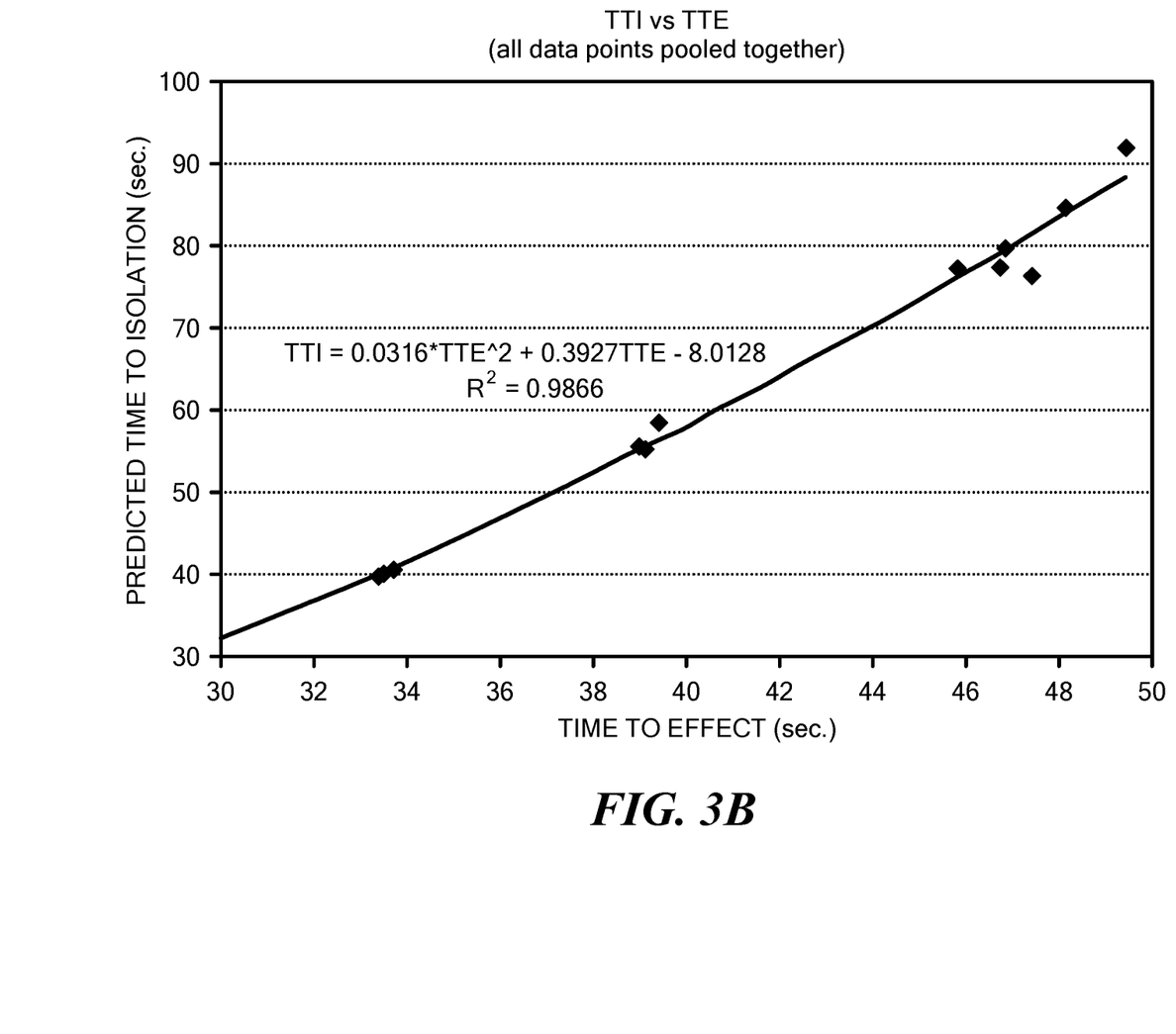
FIG. 3B shows a chart comparing exemplary TTE and TTI data, with all data points pooled together.
Figure 4:
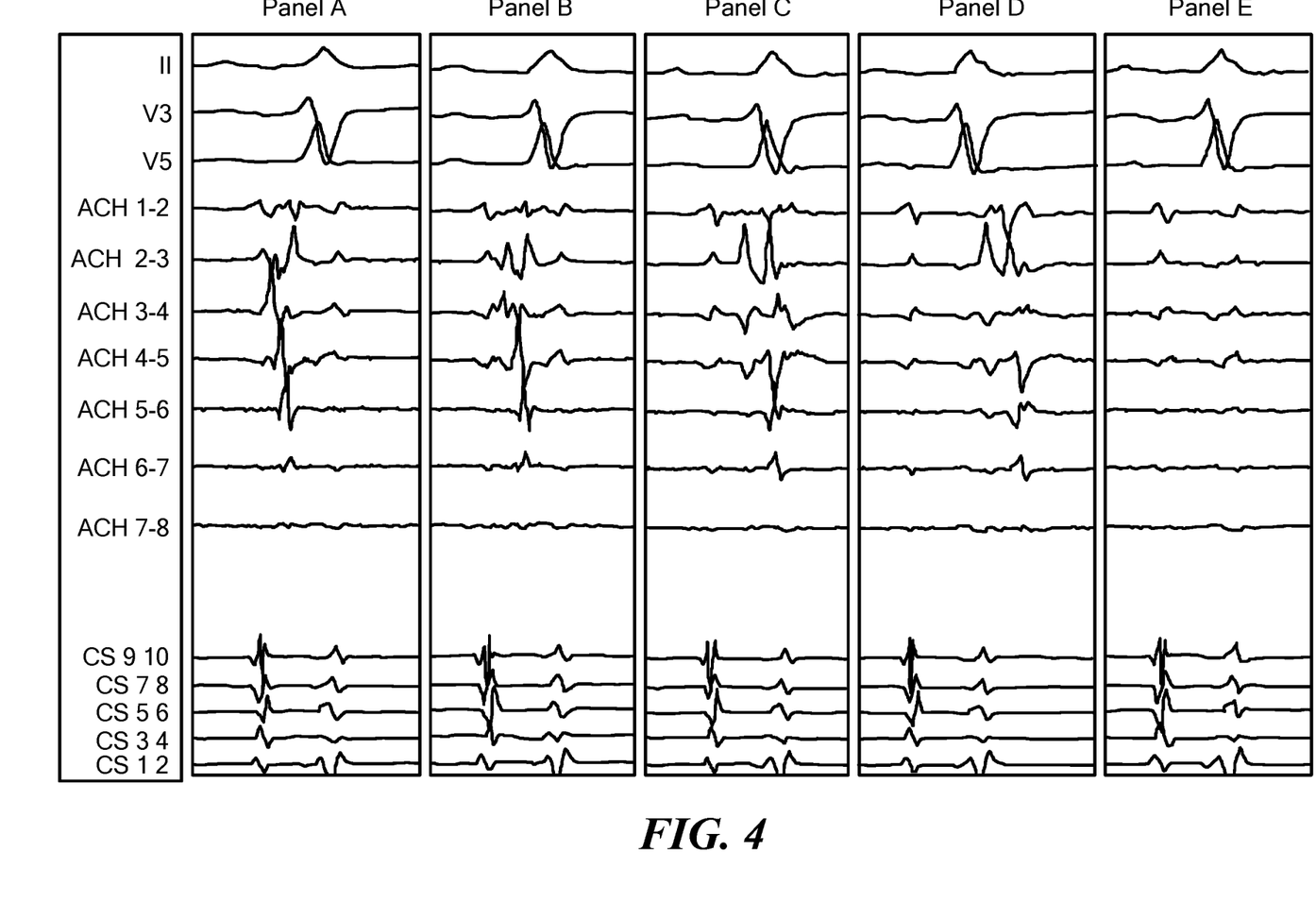
FIG. 4 shows electrograms between the left atrium and the pulmonary vein, with the electrograms changing as the pulmonary vein is isolated.

Referring now to FIGS. 3A-4, various charts are shown that illustrate the relationship between tissue thickness, TTE, TTI, and optimum cryoablation dose. As discussed in the Background section, time to effect (TTE) may be defined as the time it takes for tissue to stop conducting electricity. This is known to occur when all the conducting tissue around the ablation site has reached a temperature below approximately +23° C. (±2° C.). There is no minimum amount of tissue required as TTE will occur once all conducting fibers have reached approximately +23° C. across the depth all around the pulmonary vein at one section point, preferably near the ostium, where the pulmonary vein connects to the left atrium. In other words, TTE occurs once a circumferential annulus of approximately +23° C. or less is created up to the depth of the last conducting fiber. As estimated using computational modeling on various pulmonary vein thicknesses in idealized conditions, the observed trends between tissue thickness, TTE, and TTI are shown in FIGS. 3A and 3B.

As shown in the figures, the thicker the area of tissue (or the deeper the deepest conducting fiber is located), the longer the TTE. For reference, an average vein thickness may be approximately 1.2 mm, a thinner-than-average vein thickness may be approximately 0.5 mm, and a thicker-than-average vein thickness may be approximately 2.0 mm.

It has been determined that a cell may be ablated with a success rate of at least 75% by temperatures of approximately −20° C. (±5° C.), which may be referred to as permanent isolation. The amount of cryoablation required, in seconds, to reach permanent isolation may be referred to as the time to isolation (TTI). Similar relationships between TTE and tissue thickness exist between TTI and tissue thickness. The data shown in FIGS. 3A and 3B was obtained by experimentation. For each tissue thickness, three application forces were used (structural analysis with 10 gm, 30 gm, and 50 gm of pressure applied to the treatment element against the pulmonary vein), resulting in nine combinations. Heat transfer analysis, based on the deformed geometry, was conducted for each of the nine combinations to measure TTE and TTI (assuming TTE occurs at +23° C. and TTI occurs at −20° C.). Each cluster of data points represents one tissue thickness analyzed with three different forces.

As shown in FIGS. 3A and 3B, the TTE may be correlated to the TTI for a given tissue thickness, and the trend may also apply to non-PV tissue as well. As TTE is generally known to occur when all conducting tissue around the ablation site has reached a temperature below approximately +23° C., it can be assumed that the tissue has reached a temperature below approximately +23° C. when no more, or sufficiently attenuated or delayed, electrical signals (for example, electrograms) are obtained by the sensing device 14. Consequently, the processor 52 may determine TTE has occurred when the electrical signals received from the sensing device 14 are delayed, absent, or below a predetermined threshold. For example, the processor 52 may be configured to determine TTE has occurred when the number of electrical signals received from the sensing device 14 during a procedure are reduced such that no electrical signals are received. Additionally or alternatively, the processor 52 may be configured to determine TTE has occurred when electrical signals are received from the sensing device 14 during a procedure, but the received electrical signals show the typical electrogram signal ≥(such as the P, Q, R, S, T, and/or U waves) has been altered or affected, or is otherwise weaker than a typical electrogram signal. For example, the one or more processors 52 may be configured to determine TTE has occurred when the electrical signals received from the sensing device 14 during a procedure has an amplitude that has decreased by approximately half of a normal amplitude (e.g., decreased by 6 dB) or when the time between signal peaks increases by more than 20% of a peak-to-peak time interval prior to the start of cryotherapy delivery. As a non-limiting example, FIG. 4 shows from left to right typical panels of electrograms between the left atrium and the pulmonary vein as the cryoablation progresses. Panel A shows full-amplitude electrograms. The electrograms become progressively more attenuated from Panels B-D, and Panel E shows electrograms recorded after isolation of the pulmonary vein (which may be referred to as conduction block or electrical isolation). TTE occurs between Panels D and E. If the one or more processors 52 determine that the TTE has not occurred after a predetermined threshold of time, the one or more processors 52 may determine a recommended cryoablation dose based on this delay. For example, a maximum dose of three minutes could be recommended by the one or more processors 52. Additionally or alternatively, the one or more processors 52 may communicate to the user a suggestion (that is, generate a suggestion) that the treatment element 18 be repositioned if the one or more processors 52 determine that the TTE has not occurred after a predetermined threshold of time.

The TTI may then be determined based on TTE, in seconds, without the need for measuring or monitoring tissue temperature during the procedure and without the need for using costly, complicated, or time-consuming anatomical mapping techniques to determine the tissue depth.

The optimum cryoablation dose may be based on TTI, which may, in turn, be based on TTE. For example, if it takes approximately 39 seconds for signals transmitted by the sensing device 14 to the control unit 16 to indicate TTE (or an absence or acceptable mitigation of electrical conduction within the target tissue), the one or more processors 52 may use that data to determine a TTI of approximately 58 seconds. In other words, it can be determined based on TTE that it would take approximately 58 seconds of cryoablation to achieve at least 75% cell death, or permanent isolation. This period of cryoablation delivery may be referred to as the "dose." Thus, if it takes approximately 39 seconds for an indication of TTE, the optimum dose of cryoablation required to achieve permanent isolation would be approximately 58 seconds, or 19 seconds beyond TTE. This may then be communicated to the user or automatically carried out by the system. The equation used by the one or more processors 52 for the correlation is:

$$TTI = 3.16E\text{-}02 * TTE^2 + 3.93E\text{-}01 * TTE - 8.01E\text{+}00, \quad (1)$$

where $$R^2 = 9.87E\text{-}01 \quad (2)$$

TTE and TTI are in seconds. FIG. 3B is a non-limiting example of Equation (1) used in practice, in this case with the ARCTIC FRONT ADVANCE® 28 mm catheter (Medtronic CryoCath LP, Canada). The equation used in FIG. 3B is:

$$TTI = 0.0316 * TTE^2 + 0.3927 TTE - 8.0128 \quad (3)$$

where $$R^2 = 0.9866. \quad (4)$$

Figure 5:
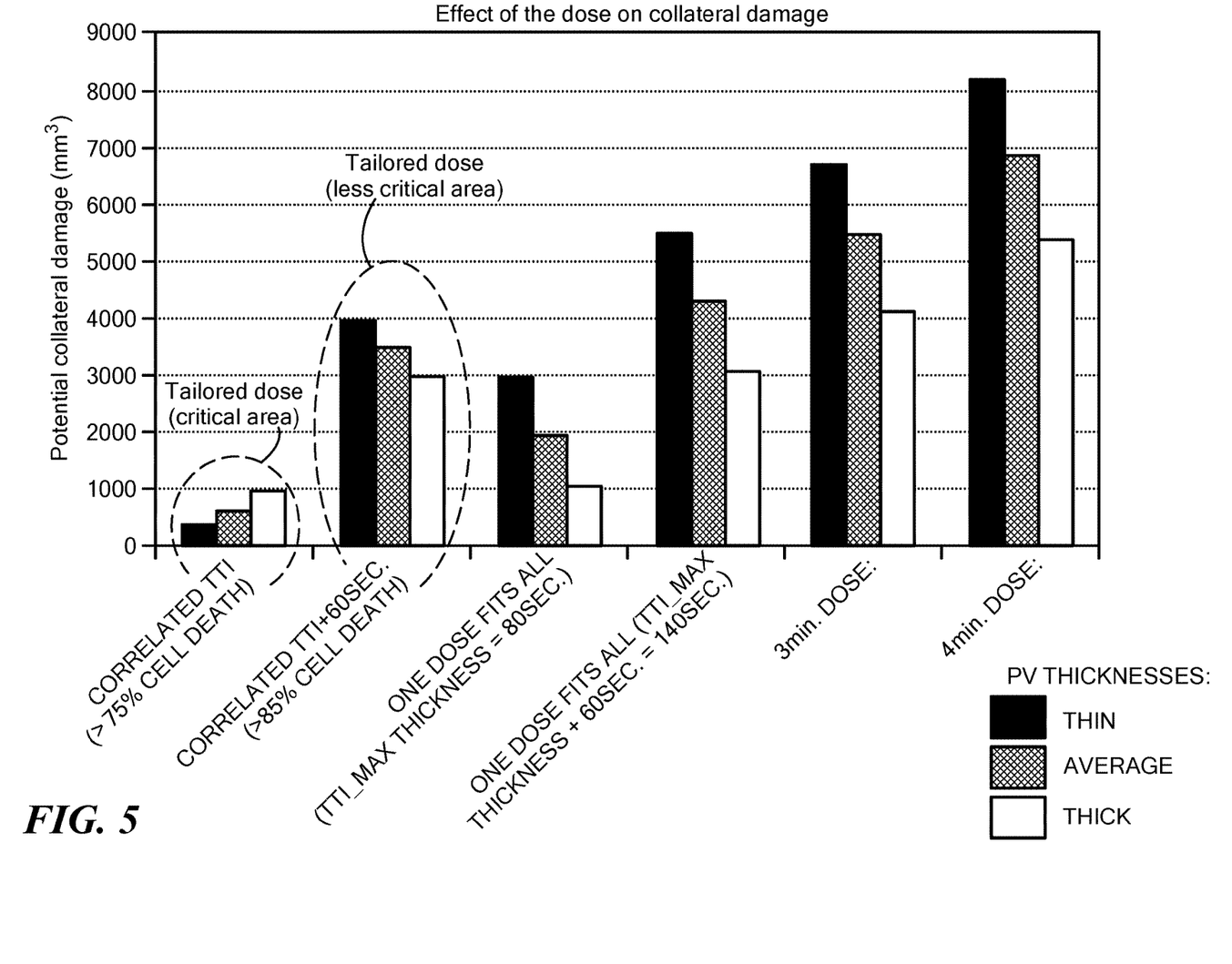
FIG. 5 shows a chart comparing the cryoablation dose to collateral damage.

When ablating areas of tissue that are thin, close to critical non-target structures (such as the phrenic nerve), or are otherwise sensitive to thermal treatment, a TTI of 75% may be acceptable to minimize the risk of collateral damage to non-target tissues. Under other circumstances, such as when ablating a relatively thicker area of tissue or an area that is well separated from critical non-target structures, increased cell death may be preferable. In this case, a dwell time may be added to the optimum dose. For example, a dwell time of approximately 60 seconds may be added to the dose to achieve at least 85% cell death. So, in the example above, the one or more processors 52 may add 60 seconds to the determined TTI of approximately 58 seconds to arrive at a recommended dose of 118 seconds, which may then be communicated to the user or automatically implemented by the system. Still further, after the recommended dose for at least 75% (or at least 85%) cell death has been delivered, the one or more processors 52 may calculate a second (subsequent) dose to achieve at least 95% cell death within the area of tissue. FIG. 5 shows exemplary data regarding the effect of the delivered dose on collateral damage. As a non-limiting example, the dose may be extended by approximately one minute once transmurality is achieved to further increase cell death in the periphery of the ablated tissue area. This second cryoablation dose may be performed as part of a freeze-thaw-freeze cycle. In other words, the first cryoablation dose may be delivered and the treatment element 18 may be allowed to warm by stopping or reducing the flow of coolant within the treatment element 18. After this thaw period, the second cryoablation dose may be delivered to the tissue. The thaw period may be defined by the length of time it takes for the tissue to, on its own, reach a temperature between approximately −5° C. and approximately −40° C. and, optionally, to remain at that temperature for a predetermined period of time. The thaw period, and optionally multiple freeze-thaw cycles, favors the solute effect, whereby large ice crystals form around the tissue cells upon slow freezing, as experienced by the cells in the periphery of the ablation lesion. As the ice crystals form, the remaining solution around the cells becomes increasingly hypertonic. This, in turn, causes the cells to shrink by the release of water (dehydration) to maintain osmotic equilibrium. The cellular damage is created upon thawing. As the ice surround the cells melts, it becomes increasing hypotonic. This high concentration of solute in the cells creates a strong pressure gradient across the cell membrane that forces a large intake of water from the extracellular environment, which is detrimental to cell structure. This is known to be the major contributor to cell destruction in the periphery of an area of ablated tissue.

However, it will be understood that the TTE and TTI values in seconds are approximate (for example, ±1 second) and may vary by patient, cryoablation system used, and/or contact between the tissue and the treatment element. For example, the data shown in FIGS. 3A and 3B were achieved using a cryoablation device, the ARCTIC FRONT ADVANCE® 28 mm device (Medtronic CryoCath LP, Canada). Although data may be different for different devices, the trends in tissue thickness and TTE and TTI, and the correlation between TTE and TTI, may be similar when using other balloon devices of comparable sizes. As a general rule, however, the less the thermal effect a device has on the target tissue, the higher the TTE and TTI values may be.

Referring now to FIG. 4, a chart comparing the cryoablation dose to collateral damage is shown. As discussed above, using a specific cryoablation dose, as calculated using the correlations described above, may reduce the risk of collateral damage to non-target tissue. For example, cryoablation is typically delivered in 3- or 4-minute doses. However, such blindly applied doses may significantly increase the amount of potential collateral damage (expressed in FIG. 4 in $m^3$) over using a dose that is based on TTE. A cryoablation dose that is equal to TTI in seconds to achieve at least 75% cell death, based on TTE, may produce the least collateral damage. Further, although it may sometimes be desirable to use a cryoablation dose that is equal to TTI+60 seconds to achieve at least 85% cell death (or up to at least 95% cell death), based on TTE, this may increase the risk of collateral damage. A "one dose fits all" approach may be used that uses the maximum TTI for the given cryoablation device 12 based on tissue thickness, regardless of actual tissue thickness or signals obtained by the sensing device 14. Although this may still cause less potential collateral damage than a 3- or 4-minute does, it may case more potential collateral damage than using a dose that is based on TTE.

Once the processor 52 determines TTE, the processor 52 may calculate a recommended cryoablation dose based on TTE and the computer may display that information to the user. The user may then accept the recommended dose or reject the recommended dose and operate the system manually or semi-automatically. Once the processor 52 determines TTI has been reached, based on signals received from the sensing device 14 and calculated TTE, the processor 52 may automatically reduce or eliminate the flow of coolant into the cryoablation device 12 or may otherwise initiate a thawing phase to break cryoadhesion between the treatment element 18 and the tissue if the user has accepted the recommended dose. Alternatively, the computer 50 may display or communicate to the user (for example, by a visual or audible alert) that electrical isolation has been achieved and the user may manually end the procedure or decide to continue the procedure. Additionally or alternatively, the system may automatically implement the recommended cryoablation dose by automatically adjusting the flow of coolant during a treatment to achieve the recommended dose. Alternatively, the same may be done on an optional computer 64 that is in communication with but separate from the system. For example, the signal from the device may be sent to the separate computer 64, which may analyze the data and propose a dose to the user based on the equations shown above. For example, the computer 64 may be in wired or wireless communication with the console 16.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A cryoablation method comprising:
   establishing a time to effect (TTE) based upon a duration of time that it takes for tissue to stop conducting electricity;
   electrically mapping signals from an area of tissue, determining the TTE from the electrical mapping signals, the electrical mapping signals including at least one electrogram signal;
   determining a recommended cryoablation dose based on the TTE; and
   adjusting a temperature of a treatment element based on the recommended cryoablation dose.

2. The method of claim 1, further comprising determining a time to isolation (TTI) based on the TTE.

3. The method of claim 2, wherein the recommended cryoablation dose is the amount of cryoablation, in seconds, required to achieve TTI.

4. The method of claim 3, wherein TTI is the time, in seconds, it takes for an area of tissue to reach −20° C.

5. The method of claim 3, wherein TTI is the time, in seconds, it takes to achieve at least 75% cell death.

6. The method of claim 1, further comprising delivering a second cryoablation dose after a warming period.

7. A method of thermal treatment comprising:
   sensing electrical mapping signals of cardiac tissue and calculating a time to effect (TTE) based upon a duration of time it takes for tissue to stop conducting electricity, determining the TTE from the electrical mapping signals including at least one electrogram signal; and
   ablating cardiac tissue with an ablation dose time determined by the TTE.

8. The method of claim 7, where the thermal treatment includes cryoablation.

9. A method of treating tissue, the method comprising:
   monitoring electrical signals from a sensing device, the electrical signals including at least one electrogram signal;
   determining a time duration from when the electrical signals received from the sensing device are at least one from the group consisting of delayed, absent, and below a predetermined threshold;
   determining a recommended thermal treatment based upon the time duration;
   initiating a thermal treatment based upon the time duration; and
   adjusting a temperature of a treatment element based on the recommended thermal treatment.

10. The method of claim 9, wherein the time duration for delayed electrical signals received from the sensing device is from when electrical signals are initially received from the sensing device to when no electrical signals are received from the sensing device.

11. The method of claim 9, wherein each electrical signal has an amplitude, the time duration for the predetermined threshold is when the electrical signals are initially received from the sensing device with a first amplitude and when the sensing device determines that the amplitude has decreased by approximately half of the first amplitude.

12. The method of claim 11, wherein the amplitude has decreased by approximately half of the first amplitude when the amplitude has decreased by 6 decibels.

13. The method of claim 9, wherein each electrical signal received from the sensing device has a signal peak, determining the time duration from when from when electrical signals are initially received from the sensing device to when a time period between signal peaks increases by more than 20%.

14. The method of claim 9, further comprising initiating the thermal treatment where the electrical signals received from the sensing device are not delayed, absent, or below a predetermined threshold.

15. The method of claim 14, wherein the thermal treatment is initiated for three minutes.

* * * * *